United States Patent [19]
Walker

[11] Patent Number: 5,608,074
[45] Date of Patent: Mar. 4, 1997

[54] PROCESS FOR THE SYNTHESIS OF 5-AMINO TETRAZOLE DERIVATIVES

[75] Inventor: Jonathan Walker, Holland, Mich.

[73] Assignee: Warner-Lambert Company, Morris Plains, N.J.

[21] Appl. No.: 359,139

[22] Filed: Dec. 19, 1994

Related U.S. Application Data

[62] Division of Ser. No. 162,519, Dec. 3, 1993, Pat. No. 5,426,191.

[51] Int. Cl.$^6$ .................................................. C07D 409/12
[52] U.S. Cl. ........................ 548/251; 549/51; 549/54; 549/57
[58] Field of Search .................................................. 548/251

[56] References Cited

FOREIGN PATENT DOCUMENTS

| | | |
|---|---|---|
| 0187487 | 7/1986 | European Pat. Off. . |
| 0299457 | 1/1989 | European Pat. Off. . |

OTHER PUBLICATIONS

Journal of Heterocyclic Chemistry, vol. 23, No. 5, Sep. 1986, pp. 1571–1577.
Liebigs Annalen der Chemie, No. 9, Sep.1980, pp. 1424–1427.
J. of Medicinal Chemistry, 35:958–965 (1992) D. T. Connor, et al.
J. of Heterocyclic Chemistry, 8:711–714 (1971) Wright, W. B., Jr. and Brabander, H. J.
J. of Heterocyclic Chemistry, 23:1571–1577 (1986) Pakray, S. and Castle, R. N.

*Primary Examiner*—David B. Springer
*Attorney, Agent, or Firm*—Francis J. Tinney

[57] ABSTRACT

An improved process for the preparation of 3-chlorobenzo[b]thiophene-2-carbonyl chlorides is described where a cinnamic acid is converted in the presence of thionyl chloride and a 4-N,N'-disubstituted aminopyridine in one step to the desired product.

8 Claims, No Drawings

PROCESS FOR THE SYNTHESIS OF 5-AMINO TETRAZOLE DERIVATIVES

This is a Divisional application of U.S. Ser. No. 08/162,519, filed Dec. 3, 1993, now U.S. Pat. No. 5,426,191.

BACKGROUND OF THE INVENTION

U.S. Pat. No. 4,703,053, which is herein incorporated by reference, discloses novel benzothiophene and benzofuran derivatives having antiallergy activity.

Connor D. T., et al., *J. of Medicinal Chemistry*, 35:958–965 (1992) discloses a series of novel benzothiophene, benzofuran, and naphthalenecarboxamidotetrazoles as antiallergy agents.

Particularly valuable as an antiallergic agent is 5-methoxy-3-(1-methylethoxy)-N-1H-tetrazol-5-yl-benzo[b]thiophene-2-carboxamide, sodium salt. This compound has also been shown to be useful as an antiasthmatic and gastric cytoprotective as well as an agent for treating rhinitis and inflammatory bowel disease.

5-Methoxy-3-(1-methylethoxy)benzo[b]thiophene-2-carboxylic acid is a key intermediate in the preparation of 5-methoxy-3-(1-methylethoxy)-N-1H-tetrazol-5-yl-benzo[b]thiophene-2-carboxamide, sodium salt. This key intermediate, in turn, is prepared as disclosed in U.S. Pat. No. 4,703,053 in seven steps from 5-methoxysalicylic acid.

U.S. Pat. Nos. 4,910,317 and 4,931,459 disclose novel benzothiophene and benzofuran derivatives having antiallergy activity. Benzo[b]-thiophene-2-carboxylic acids, which are key intermediates for preparing these compounds, are prepared from 3-chlorobenzo[b]thiophene-2-carbonyl chlorides. The previous acid chlorides, in turn, are prepared from cinnamic acids using methodology disclosed by Wright W. B., Jr. and Brabander H. J., *J. of Heterocyclic Chemistry*, 8:711–714 (1971) and Pakray S. and Castle R. N., *J. of Heterocyclic Chemistry*, 23:1571–1577 (1986). Thus, the appropriate cinnamic acid is converted to a 3-chlorobenzo[b]thiophene-2-carbonyl chloride using thionyl chloride and pyridine. However, the yields of acid chloride are low and the procedure is difficult to conduct on a large scale.

We have surprisingly and unexpectedly found an improved procedure in which a cinnamic acid can be converted to a 3-chlorobenzo[b]thiophene-2-carbonyl chloride with thionyl chloride and 4-dimethylaminopyridine (DMAP). The process is general and affords high yields of the 3-chlorobenzo[b]thiophene-2-carbonyl chlorides. Additionally, the present process affords significant advantages compared to the previous procedures that make it amenable to a large-scale industrial synthesis. Thus, the DMAP is charged as a solid together with the cinnamic acid, thereby eliminating the slow "metering-in" of liquid pyridine. Also, the DMAP process is far more robust compared to the previous procedures. The pyridine process is very time dependent requiring close monitoring of the reaction. Extended reaction times cause significant yield reductions. Extended reaction times of 8 hours or more in the DMAP process do not cause any significant reductions in yields or purities. Furthermore, DMAP hydrochloride is filtered as a solid after extraction of the reaction mixture with a solvent, thereby eliminating previous hot extraction of the molten pyridinium hydrochloride layer with an organic solvent. The recovered DMAP hydrochloride may be reused directly in subsequent reactions without detriment to the chemical yield or purity. Finally, solid DMAP hydrochloride poses fewer waste disposal problems than the molten pyridinium hydrochloride from the pyridine process. DMAP hydrochloride is water soluble and is dissolved by recirculating water through the filter before disposal, in contrast to the slow quench of the molten layer into water.

The object of the present invention is an improved, efficient, environmentally safe and economical process for the preparation of 3-chlorobenzo-[b]thiophene-2-carbonyl chlorides. Additionally, a second object of the present invention is an improved, efficient, and economical process for the preparation of 5-methoxy-3-(1-methylethoxy)-N-1H-tetrazol-5-yl-benzo[b]thiophene-2-carboxamide, sodium salt.

SUMMARY OF THE INVENTION

Accordingly, a first aspect of the present invention is a process for the preparation of a compound of Formula IV

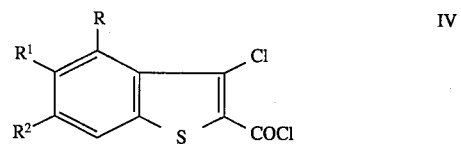

wherein R, R¹, and R² are each independently H, alkyl, alkoxy, halogen, or nitro which comprises treating a compound of Formula V

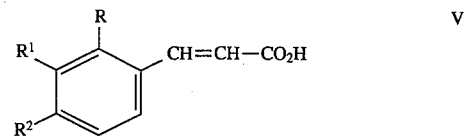

wherein R, R¹, and R² are as defined above with thionyl chloride in the presence of a 4-N,N'-disubstituted aminopyridine and a solvent to afford a compound of Formula IV.

A second aspect of the present invention is an improved process for the preparation of the compound of Formula I

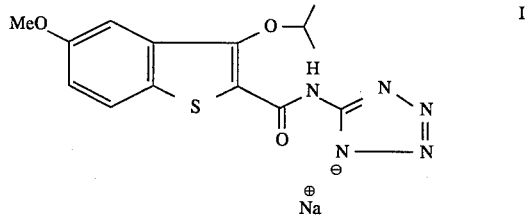

which comprises Step (a) treating the compound of Formula Va

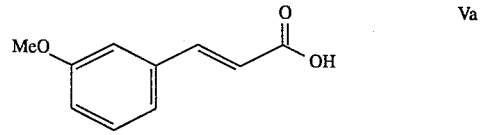

with thionyl chloride in the presence of a 4-N,N'-disubstituted aminopyridine and a solvent to afford the compound of Formula IVa;

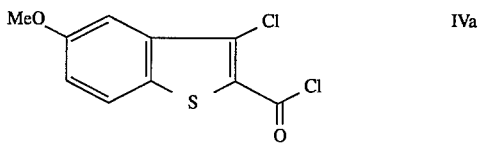

Step (b) treating the compound of Formula IVa with sodium isopropoxide in a solvent followed by saponification with a base to afford the compound of Formula III;

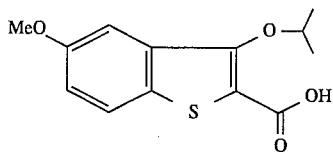

Step (c) treating the compound of Formula III with thionyl chloride and pyridine in a solvent and subsequently adding 5-aminotetrazole and triethylamine in a solvent to afford the compound of Formula II;

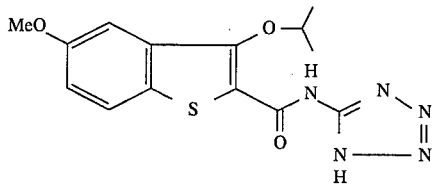

Step (d) treating the compound of Formula II with sodium hydroxide solution in a solvent to afford the compound of Formula I.

DETAILED DESCRIPTION OF THE INVENTION

In this invention, the term "alkyl" means a straight or branched hydrocarbon group having from 1 to 10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like.

The term "alkoxy" means O-alkyl as defined above for alkyl.

"Halogen" is iodine, bromine, chlorine, and fluorine.

The process of the present invention, in its first aspect, is a new, improved, economical, and commercially feasible method for preparing 3-chlorobenzo-[b]thiophene-2-carbonyl chlorides. The process of the present invention in its first aspect is outlined in Scheme 1:

SCHEME 1

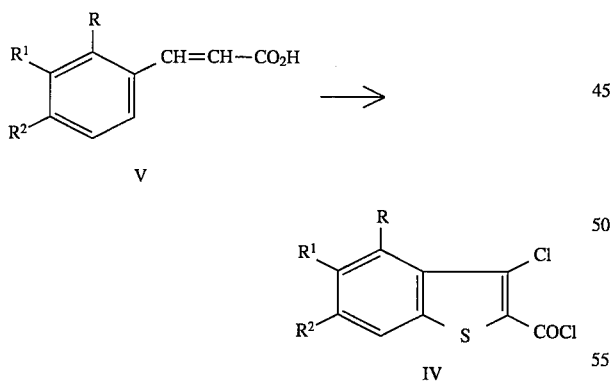

A compound of Formula IV wherein R, $R^1$, and $R^2$ are each independently H, alkyl, alkoxy, halogen, or nitro is prepared by treating about one equivalent of a compound of Formula V wherein R, $R^1$, and $R^2$ are as defined above at about 80° C. to about 85° C. with about 0.2 to about 1 equivalent of a 4-N,N'-disubstituted aminopyridine or a hydrochloride salt thereof such as, for example, 4-(4-methyl-1-piperidinyl)pyridine, 4-dimethylaminopyridine (DMAP), 4-(4-methyl-1-piperidinyl)pyridine hydrochloride, DMAP hydrochloride and the like and about 3 to about 10 equivalents of thionyl chloride in a solvent such as, for example, heptane and the like for about 5 to about 7 hours and subsequent extraction with a solvent such as, for example, toluene, ethyl acetate, and the like, to remove the 4-N,N'-disubstituted aminopyridine hydrochloride and addition of a nonpolar solvent such as, for example, heptane to crystallize a compound of Formula IV. Preferably, the reaction is carried out with about one equivalent of a compound of Formula V at about 80° C. to about 85° C. with about one equivalent of DMAP and about five equivalents of thionyl chloride in heptane for about 5 to about 7 hours and subsequent extraction with ethyl acetate to remove DMAP hydrochloride and crystallization of a compound of Formula IV by addition of heptane.

The process of the present invention, in its second aspect, is a new, improved, economical, and commercially feasible method for preparing 5-methoxy-3-(1-methylethoxy)-N-1H-tetrazol-5-yl-benzo[b]-thiophene-2-carboxamide, sodium salt.

The process of the present invention, in its second aspect, is outlined in Scheme 2:

SCHEME 2

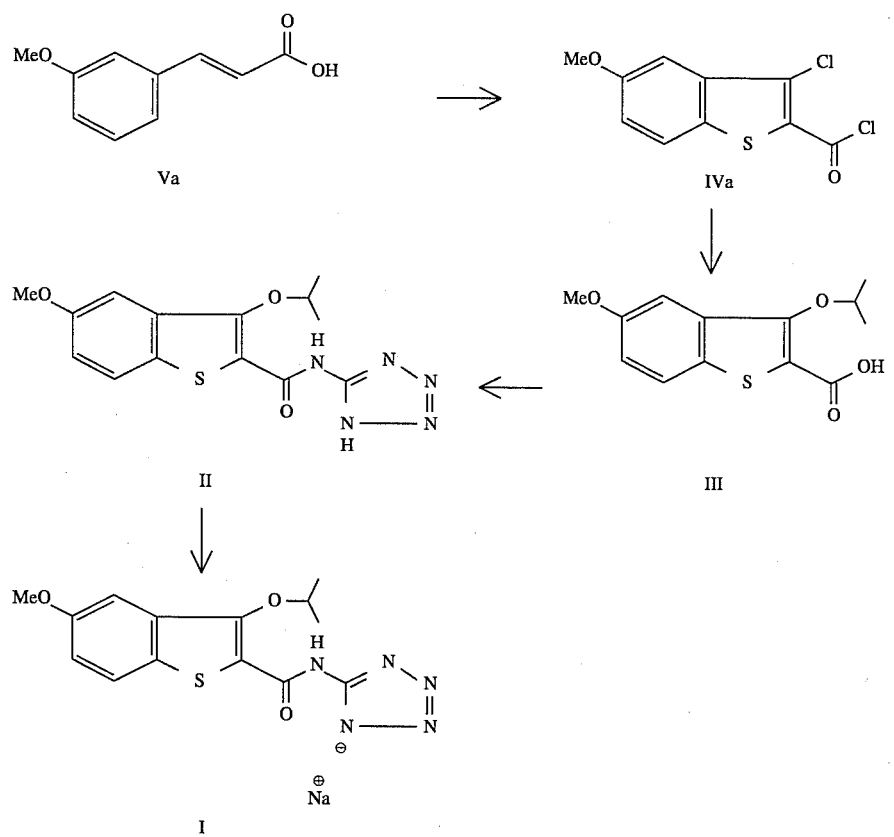

The compound of Formula IVa is prepared from the compound of Formula Va as previously described using the methodology for converting a compound of Formula V to a compound of Formula IV.

The compound of Formula III is prepared by treating the compound of Formula IVa in a solvent such as, for example, tetrahydrofuran (THF) and the like in the presence of sodium isopropoxide followed by saponification with a base such as, for example, sodium hydroxide and the like to afford the compound of Formula III. Preferably, the reaction is carried out in THF followed by saponification with sodium hydroxide.

The compound of Formula II is prepared by treating the compound of Formula III in a solvent such as, for example, acetonitrile and the like in the presence of thionyl chloride and pyridine followed by 5-aminotetrazole and triethylamine to afford the compound of Formula II. Preferably, the reaction is carried out in acetonitrile. The use of thionyl chloride and pyridine for the preparation of the compound of Formula II from the compound of Formula III avoids the expensive coupling reagent, N,N'-carbonyldiimidazole, disclosed by Connor D. T., et al., *J. of Medicinal Chemistry*, 35:958–965 (1992).

The compound of Formula I is prepared by treating the compound of Formula II in a solvent such as, for example, isopropanol and the like with sodium hydroxide to afford the compound of Formula I. Preferably, the reaction is carried out in isopropanol.

Compounds of Formula V and Formula Va are either known or capable of being prepared by methods known in the art.

Connor D. T., et al., *J. of Medicinal Chemistry*, 35:958–965 (1992) discloses the use of 3-chlorobenzo[b]thiophene-2-carbonyl chlorides in the preparation of benzo[b]thiophene derivatives and in particular in the preparation of 5-methoxy-3-(1-methylethoxy)-N-1H-tetrazol-5-yl-benzo[b]thiophene-2-carboxamide, sodium salt which is disclosed as an antiallergy agent.

The following examples are illustrative to show the present process, the preparation of starting materials, and the use of 3-chloro-5-methoxybenzo[b]thiophene-2-carbonyl chloride to prepare the key intermediate, 5-methoxy-3-(1-methylethoxy)benzo[b]thiophene-2-carboxylic acid, in the synthesis of 5-methoxy-3-(1-methylethoxy)-N-1H-tetrazol-5-yl-benzo[b]thiophene-2-carboxamide, sodium salt useful as an antiallergy agent.

EXAMPLE 1

3-Chloro-5-methoxybenzo[b]thiophene-2-carbonyl chloride

To a 12 L 3-necked round-bottomed flask fitted with a mechanical stirrer, a thermometer, an addition funnel, and a reflux condenser with a nitrogen inlet are charged 3-methoxycinnamic acid (320 g), 4-dimethylaminopyridine (DMAP) (219.5 g) and heptane (800 mL). The slurry is heated to 50° C. with stirring under nitrogen and to this is added thionyl chloride (1.07 kg) via the addition funnel over 30 minutes. (The rate of addition is controlled so as to maintain a steady rate of evolution of gases.) The mixture is heated at reflux (82° C.) for 5.5 hours after which ethyl acetate (3.6 L) preheated to 70° C. is charged to the flask.

The suspension is heated at reflux for a further 30 minutes and then filtered through a sintered glass funnel into a 12 L 3-necked round-bottomed flask fitted with a mechanical stirrer, a thermometer and a reflux condenser. The filter cake (the filter cake is dried in a vacuum oven at 60° C. to give 280.2 g (98.3% recovery) of recovered DMAP hydrochloride) is washed with ethyl acetate (1.2 L), preheated to 70° C., and the combined filtrates are cooled to 40° C. with stirring at which point crystallization occurs. Heptane (3.6 L) is charged to the flask and the slurry is cooled to room temperature and stirred under nitrogen for 16 hours. The slurry is cooled to 0° C. to 5° C. and stirred for 2 hours and then the yellow solids are collected on filter paper using a Buchner funnel. The filter cake is washed with heptane (1 L), precooled to 0° C. to 5° C. and then dried in a vacuum oven at 60° C. to give 235.5 g of the title compound as a bright yellow solid; Vapor Phase Chromatography (VPC) 92.6% (by area).

Infrared Spectroscopy (IR) (cm$^{-1}$, 1% KBr pellet): 1767; Nuclear Magnetic Resonance Spectroscopy ($^1$H NMR) (δ, CDCl$_3$, 200 MHz): 7.70 (d, 1H, J=8.8 Hz), 7.32–7.23 (m, 2H), 3.93 (s, 3H, CH$_3$); Mass Spectroscopy (MS) (m/z): 260 (M$^+$), 225 (M—Cl)$^+$, 210 ((M—Cl—CH$_3$)$^+$), 197 ((M—COCl)$^+$);

The following general procedure is used to prepare Examples 2 to 10.

Thionyl chloride (81.9 mL, 1.12 mol) is added over 10 minutes to a white slurry of the cinnamic acid (0.22 mol), DMAP (27.4 g, 0.22 mol), and hexane (100 mL) heated to 50° C. The exothermic reaction with accompanying SO$_2$ evolution forms a mixture varying in color from orange to brown which is stirred at 60° C. for 15 minutes and then heated to reflux (80°–85° C.) for 5 to 7 hours. The reaction is quenched by addition of hot ethyl acetate (450 mL) and an additional hour of refluxing. DMAP-HCl precipitates out of solution and is removed via hot filtration through a sintered-glass funnel and washed with hot ethyl acetate (150 mL). The product is isolated from the filtrates as described for each compound. Recrystallizations are carried out on 5 g to 10 g samples of compounds in order to obtain material for spectroscopic analysis.

EXAMPLE 2

3-Chlorobenzo[b]thiophene-2-carbonyl chloride

Heptane (450 mL) is added to the filtrates. Ethyl acetate (600 mL) is then removed by vacuum distillation and replaced by heptane (595 mL) to form an orange slurry which is cooled to 0° C. for 1 hour. The product is isolated by filtration and dried in a 55° C. vacuum oven to give 25.9 g of the title compound. An off-white solid is obtained after two methylene chloride (CH$_2$Cl$_2$)/hexane recrystallizations;

IR (cm$^{-1}$, 1% KBr pellet): 1770; $^1$H NMR (δ, CDCl$_3$, 200 MHz): 8.06–7.99 (m, 1H), 7.91–7.84 (m, 1H), 7.67–7.51 (m, 2H); MS (m/z): 230 (M$^+$), 195 ((M—Cl)$^+$), 167 ((M—COCl)$^+$), 132 ((M—COCl$_2$)+).

EXAMPLE 3

3-Chloro-6-methoxybenzo[b]thiophene-2-carbonyl chloride

Heptane (300 mL) is added to the filtrate solution which is then cooled slowly to 0° C. Additional heptane (100 mL) is used to precipitate product out of solution. The slurry is stirred for an additional hours at 0° C. The product is isolated by filtration and dried in a 55° C. vacuum oven to give 25.3 g of the title compound. A tan solid is obtained by recrystallization from CH$_2$Cl$_2$/hexane;

IR (cm$^{-1}$, 1% KBr pellet): 1780; $^1$H NMR (δ, CDCl$_3$, 200 MHz): 7.87 (d, J=9.1 Hz, 1H, H-4), 7.22 (d, J=2.2 Hz, 1H, H-7), 7.14 (dd, J=9.1 Hz, 2.2 Hz, 1H, H-5), 3.93 (s, 3H, CH$_3$); MS (m/z): 198 ((M—COCl)$^+$), 183 ((M—COCl—CH$_3$)$^+$).

EXAMPLE 4

3-Chloro-6-nitrobenzo[b]thiophene-2-carbonyl chloride

The filtrates are allowed to cool slowly to room temperature and some product begins to precipitate out of solution. Heptane (450 mL) is added to the yellow slurry which, after an additional 1 hour of stirring, is cooled to 0° C. for 2 hours. The product is isolated by filtration and dried in a 55° C. vacuum oven to give 28.5 g of the title compound. A yellow solid is obtained after two CH$_2$Cl$_2$/hexane (8:1) recrystallizations;

IR (cm$^{-1}$, 1% KBr pellet): 1795; $^1$H NMR (δ, CDCl$_3$, 200 MHz):8.82–8.81 (m, 1H, H-7), 8.42–8.37 (m, 1H, H-5), 8.21–8.17 (m, 1H, H-4); MS (m/z): 213 ((M—COCl)$^+$).

EXAMPLE 5

3-Chloro-6-methylbenzo[b]thiophene-2-carbonyl chloride

The filtrates are allowed to cool slowly to room temperature causing product to begin to form. Heptane (450 mL) is added to the yellow slurry to further precipitate out the product. After 2 hours of stirring, the slurry is cooled to 0° C. for 2 hours. Product is isolated by filtration and dried in a 55° C. vacuum oven to give 26.4 g of the title compound. A yellow solid is obtained by recrystallization from CH$_2$Cl$_2$;

IR (cm$^{-1}$, 1% KBr pellet): 1761; $^1$H NMR (δ, CDCl$_3$, 200 MHz): 7.89 (d, J=8.4, 1H), 7.63 (s, 1H), 7.36 (d, J=8.4, 1H), 2.54 (s, 3H, CH$_3$); MS (m/z): 2.44 (M$^+$), 209 ((M—Cl)$^+$).

EXAMPLE 6

3,4,6-Trichlorobenzo[b]thiophene-2-carbonyl chloride

The filtrates are allowed to cool slowly to room temperature. Subsequent addition of heptane (450 mL) causes an oil to form which is mostly dissolved by addition of ethyl acetate (250 mL). The volume of the solvent is reduced to approximately 400 mL, and the solution is cooled to 0° C. for 6 hours to obtain solid product. The product is isolated by filtration and dried in a 55° C. vacuum oven to give 25.1 g of the title compound. A pale yellow solid is obtained by recrystallization from CH$_2$Cl$_2$;

IR (cm$^{-1}$, 1% KBr pellet): 1797; $^1$H NMR (δ, CDCl$_3$, 200 MHz): 7.72 (d, J=1.8 Hz, 1H), 7.51 (d, J=1.8 Hz, 1H); MS (m/z): 235 ((M—COCl)$^+$).

EXAMPLE 7

3,4-Dichlorobenzo[b]thiophene-2-carbonyl chloride

The filtrates are allowed to cool to room temperature followed by the addition of heptane (450 mL). The resultant yellow-orange slurry is stirred for 1 hour before being cooled to 0° C. for an additional 2 hours. The product is isolated by filtration and dried in a 55° C. vacuum oven to give 22.2 g of the title compound. A pale yellow solid is obtained by recrystallization from a CH$_2$Cl$_2$/hexane solution (5:1);

IR (cm$^{-1}$, 1% KBr pellet): 1799; $^1$H NMR (δ, CDCl$_3$, 200 MHz): 7.78–7.74 (m, 1H), 7.51–7.48 (m, 2H); MS (m/z): 202 ((M—COCl)$^+$), 167 ((M—COCl$_2$)$^+$).

EXAMPLE 8

3-Chloro-5-nitrobenzo[b]thiophene-2-carbonyl chloride

As the filtrates are cooled slowly to room temperature, product begins to precipitate out of solution. Heptane (450 mL) is added to the yellow slurry which is then cooled to 0° C. for 2 hours. The product is isolated by filtration and dried in a 55° C. vacuum oven to give 30.4 g of the title compound. A yellow solid is obtained by recrystallization from CH$_2$Cl$_2$/hexane (7:1);

IR (cm$^{-1}$, 1% KBr pellet): 1799; $^1$H NMR (δ, CDCl$_3$, 200 MHz): 8.68–8.60 (m, 1H), 8.43–8.36 (m, 1H), 7.83–7.75 (m, 1H); MS (m/z): 213 ((M—COCl)$^+$).

EXAMPLE 9

3,5-Dichlorobenzo[b]thiophene-2-carbonyl chloride

All solvents are removed on a rotary evaporator and the remaining solid is redissolved in CH$_2$Cl$_2$ (500 mL) and hexane (500 mL). The total volume of the solution is reduced to approximately 300 mL and then cooled to 0° C. for 4 hours. The product is isolated by filtration and dried in a 55° C. vacuum oven to give 23.9 g of the title compound. An off-white solid is obtained by recrystallization from CH$_2$Cl$_2$;

IR (cm$^{-1}$, 1% KBr pellet): 1792; $^1$H NMR (δ, CDCl$_3$, 200 MHz): 8.04–7.96 (m, 1H), 7.65–7.50 (m, 2H); MS (m/z): 202 ((M—COCl)$^+$).

EXAMPLE 10

3,6-Dichlorobenzo[b]thiophene-2-carbonyl chloride

The filtrates are allowed to cool slowly to room temperature. Heptane (450 mL) is added to form a slurry which is cooled to 0° C. for 1 hour. Product is isolated by filtration and dried in a 55° C. vacuum oven to give 39.1 g of the title compound. The product is obtained by recrystallization from a CH$_2$Cl$_2$/hexane (9:1) solution;

IR (cm$^{-1}$, 1% KBr pellet): 1797; $^1$H NMR (δ, CDCl$_3$, 200 MHz): 7.93 (d, J=8.8 Hz, 1H, H-4), 7.84 (d, J=1.8 Hz, 1H, H-7), 7.51 (dd, J=1.8 Hz, 8.8 Hz, 1H, H-5); MS (m/z): 202 ((M—COCl)$^+$).

EXAMPLE 11

5-Methoxy-3-(1-methylethoxy)-N-1H-tetrazol-5-yl-benzo[b]thiophene-2-carboxamide, sodium salt

Step 1: Preparation of 5-methoxy-3-(1-methylethoxy)benzo[b]thiophene-2-carboxylic acid To a nitrogen purged 2 L 3-necked round-bottomed flask fitted with a mechanical stirrer, a thermometer, an addition funnel, and a reflux condenser with a nitrogen inlet are charged sodium hydride (123.6 g) and THF (965 mL). With agitation, isopropyl alcohol (IPA) (250 mL) is added cautiously via the dropping funnel over 30 minutes. (The rate of addition of IPA is adjusted to maintain a steady evolution of hydrogen gas.) The temperature of the mixture rises to 45° C., and the temperature is maintained at this value for a further 1 hour by means of a heating mantle. After this period of time, the mixture is cooled to room temperature.

To a 12 L 3-necked round-bottomed flask fitted with a mechanical stirrer, a thermometer, an addition funnel and a reflux condenser with a nitrogen inlet are charged 3-chloro-5-methoxybenzo[b]thiophene-2-carbonyl chloride (Example 1) (336 g) and THF (2.3 L). The solution of sodium isopropoxide from above is charged to the THF solution of the acid chloride in four portions causing the temperature of the reaction mixture to rise to 60° C. The flask which contains the sodium isopropoxide is rinsed with THF (275 mL) and the rinse is added to the 12 L reaction flask. The mixture is heated under reflux for 7 hours and then cooled to room temperature and stirred for 12 hours. After cooling to 5° C. to 10° C., concentrated hydrochloric acid (85 mL) is added and the dark mixture stirred for 1 hour to give a final pH of 1.5. The reaction is filtered through filter paper and the filter cake is washed with THF (200 mL). The clear filtrates are charged to a 12 L 3-necked round-bottomed flask fitted with a mechanical stirrer, a thermometer, and a distillation head with reflux condenser and THF is distilled out of the flask under low vacuum to a batch temperature of 50° C. Heptane (3.1 L) is charged to the flask and the slurry is cooled to 5° C. and filtered through filter paper. The filter cake is washed with heptane (300 mL) and the combined filtrates are washed with a sodium bicarbonate solution (3×390 mL) prepared by dissolving sodium bicarbonate (47 g) in deionized water (1170 mL). The heptane solution is charged to a 12 L 3-necked round-bottomed flask fitted with a mechanical stirrer, a thermometer, and a distillation head with reflux condenser and heptane is distilled out of the flask under low vacuum to a batch temperature of 70° C. Upon cooling, IPA (815 mL) and a solution of potassium hydroxide (392 g) in deionized water (1570 mL) are charged to the 12 L flask. The distillation head is replaced with a reflux condenser and the dark solution is heated to reflux and stirred for 4 hours and then cooled to room temperature and stirred for 16 hours. The reflux condenser is again replaced with a distillation head and IPA is distilled out at atmospheric pressure to a batch temperature of 95° C. Deionized water (1570 mL) is added to the solution which is then cooled to 5° C. to 10° C. and adjusted to pH 8 using concentrated hydrochloric acid (480 mL). The aqueous solution is extracted with methyl isobutyl ketone (MIBK) (2×500 mL) and the combined MIBK extracts are extracted with deionized water (300 mL). The aqueous solutions are combined and stirred with PWA carbon (50 g) at room temperature for 16 hours. The solution is filtered through filter paper coated with supercel and the filter cake is washed with deionized water (2×300 mL). The pale yellow filtrates are transferred to a 12 L 3-necked round-bottomed flask fitted with a mechanical stirrer and a thermometer. With agitation, the solution is cooled to 5° C. to 10° C. and concentrated hydrochloric acid (70 mL) is added to give a final pH of 2. The slurry is stirred for 2 hours at 5° C. to 10° C. and the crude product is collected on filter paper and washed with deionized water (3×400 mL). The off-white product is dried in a vacuum oven at 50° C. to afford 215.1 g of the title compound;

High Pressure Liquid Chromatography (HPLC): 99.72% (w/w); 98.93% (by area).

Optionally, the product may be recrystallized as follows: To a 5 L 3-necked round-bottomed flask fitted with a mechanical stirrer, a thermometer and a reflux condenser with a nitrogen inlet are charged crude 5-methoxy-3-(1-methylethoxy)benzo[b]thiophene-2-carboxylic acid (206 g), IPA (1.07 L), and deionized water (2.14 L) . With agitation, the slurry is heated to 80° C. to 85° C. and stirred until all the solids dissolve to give a homogeneous solution. The heating mantle is removed and the mixture is allowed to air-cool to 30° C. to 35° C. The slurry is cooled to 0° C. to 5° C. in an ice bath and stirred for 2 hours. The solid is collected on filter paper, washed with 0° C. to 5° C. deionized water (1 L), and dried in a vacuum oven at 55° C. to 60° C. to give 205 g of the title compound as an off-white solid;

HPLC: 98.25% (w/w); 99.58% (by area).

Step 2: Preparation of 5-methoxy-3-(1-methylethoxy)-N-1H-tetrazol-5-yl-benzo[b]thiophene-2-carboxamide To a nitrogen purged 3 L 3-necked round-bottomed flask fitted with a mechanical stirrer, a thermometer, a reflux condenser, and an addition funnel are charged 5-methoxy-3-(1-methylethoxy)benzo[b]thiophene-2-carboxylic acid (300 g) and acetonitrile (1.97 L). The slurry is heated to 60° C. to give a homogeneous solution. (The warm solution is filtered if particulate matter is observed.)

To a nitrogen purged 5 L 3-necked round-bottomed flask fitted with a mechanical stirrer, a thermometer, addition funnel, and a distillation head are charged thionyl chloride (268.2 g), acetonitrile (0.85 L), and pyridine (0.18 g). This solution is heated to 60° C. and to this is added the warm solution of 5-methoxy-3-(1-methylethoxy)benzo[b]thiophene-2-carboxylic acid via the addition funnel. (The rate of sulfur dioxide and hydrogen chloride gas evolution is controlled by the rate of addition of the 5-methoxy-3-(1-methylethoxy)benzo[b]thiophene-2-carboxylic acid solution to the thionyl chloride solution.) After addition of the 5-methoxy-3-(1-methylethoxy)benzo[b]thiophene-2-carboxylic solution, the reaction temperature is slowly raised to 80° C. (The solubility of sulfur dioxide and hydrogen chloride gases decrease as the temperature increases. Foaming could result if the temperature is raised too quickly.) and 1.35 L of distillate is collected. An additional charge of acetonitrile (1.13 L) is added to the reaction mixture which is then cooled to 20° C.

To a nitrogen purged 1 L 3-necked round-bottomed flask fitted with a mechanical stirrer and a thermometer are charged 5-aminotetrazole (115.1 g), acetonitrile (0.56 L), and triethylamine (136.7 g). The solution is heated to 45° C. and then added to the 5 L flask containing the acid chloride over 25 minutes. (A 23° C. exotherm results during the addition (20° C. to 43° C.)). The resulting mixture is stirred at 50° C. for 1 hour and then at 25° C. for 16 hours. (Salts precipitate out of solution while the mixture is being stirred at 50° C.). Deionized water (1.42 L) is added to the product slurry which is then cooled to 0° C. to 5° C. The solids are collected on filter paper and washed with IPA (2×400 mL) to give 545.2 g (309.7 g dry) of IPA-wet 5-methoxy-3-(1-methylethoxy)-N-1H-tetrazol-5-yl-benzo[b]thiophene-2-carboxamide as a light grey solid. The IPA-wet cake is used directly in the next step;

HPLC: 99.8% (w/w); 99.7% (by area).

Step 3: Preparation of 5-methoxy-3-(1-methylethoxy)-N-1H-tetrazol-5-yl-benzo[b]thiophene-2-carboxamide, sodium salt To a nitrogen purged 3 L 3-necked round-bottomed flask fitted with a mechanical stirrer, a thermometer, pH probe, and a reflux condenser are charged 5-methoxy-3-(1-methylethoxy)-N-1H-tetrazol-5-yl-benzo[b]thiophene-2-carboxamide (309.7 g), and IPA (1.25 L). The resultant slurry is heated to 60° C. and to this is added a solution of sodium hydroxide (38.1 g) in deionized water (307 mL) to give a final pH of 9.0. (A hazy purple solution forms after the addition of the sodium hydroxide solution). The solution is stirred at 60° C. for 30 minutes and filtered through a Celite bed. The filter cake is washed with IPA (640 mL) and the combined filtrates are charged to a 12 L 3-necked round-bottomed flask, fitted with a mechanical stirrer, a thermometer, and a distillation head, followed by additional IPA (4 L). The IPA solution is heated to reflux (81° C.) and 2.8 L of the IPA-water azeotropic mixture are distilled out of the flask. The resulting slurry is cooled to 25° C. and stirred for 18 hours and then at 0° C. to 5° C. for 2 hours. The solids are collected on filter paper and washed with IPA (3×400 mL). The filter cake is transferred to a 3 L 3-necked round-bottomed flask fitted with a mechanical stirrer, a thermometer, and a reflux condenser. Acetone (1.39 L) is charged to the flask and the slurry is heated at 50° C. for 2 hours, cooled to 25° C., and then to 0° C. to 5° C. and stirred for 1 hour. (The acetone reslurry procedure is found to effectively remove the purple color that contaminates the product.) The solids are collected on filter paper, washed with acetone (400 mL), and dried in a vacuum oven at 45° C. for 18 hours to give 274 g of 5-methoxy-3-(1-methylethoxy)-N-1H-tetrazol-5-yl-benzo[b]thiophene-2-carboxamide, sodium salt as a beige solid. An off-white final product is prepared by passing the aqueous IPA solution of 5-methoxy-3-(1-methylethoxy)-N-1H-tetrazol-5-yl-benzo[b]thiophene-2-carboxamide, sodium salt through a carbon bed prior to azeotropic removal of water.

| | |
|---|---|
| Assay (HPLC): | 99.1% (w/w) |
| | 99.8% (by area) |
| Titration (0.1N HClO$_4$): | 99.76% |
| Identity (IR): | Consistent with structure |
| Sodium Content: | 6.49% (6.47% theory) |

I claim:

1. A process for the preparation of the compound of Formula I

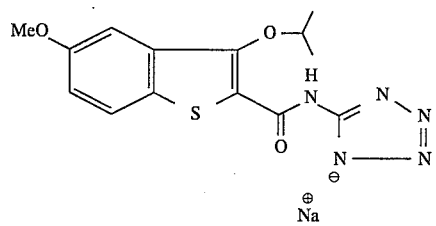

which comprises Step (a) treating the compound of Formula Va

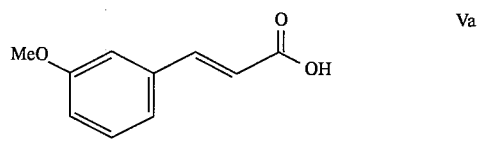

with thionyl chloride in the presence of a 4-N,N'-disubstituted aminopyridine selected from the group consisting of 4-(4-methyl-1-piperidinyl)pyridine; 4-(4-methyl-1-piperidinyl)pyridine hydrochloride; 4-dimethylaminopyridine; and 4-dimethylaminopyridine hydrochloride and a solvent to afford the compound of Formula IVa;

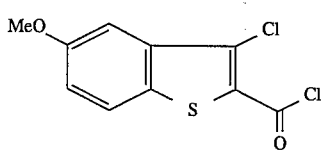

Step (b) treating the compound of Formula IVa with sodium isopropoxide in a solvent followed by saponification with a base to afford the compound of Formula III;

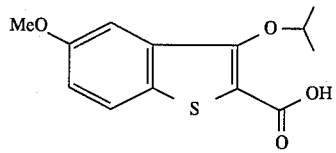

Step (c) treating the compound of Formula III in a solvent with thionyl chloride and pyridine in a solvent and subsequently adding 5-aminotetrazole and triethylamine in a solvent to afford the compound of Formula II;

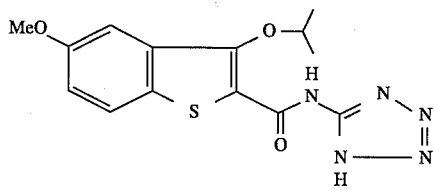

Step (d) treating the compound of Formula II with sodium hydroxide solution in a solvent to afford the compound of Formula I.

2. A process according to claim 1 wherein the 4-N,N'-disubstituted aminopyridine is 4-dimethylaminopyridine.

3. A process according to claim 1 wherein the solvent in Step (a) is heptane.

4. A process according to claim 1 wherein the solvent in Step (b) is tetrahydrofuran.

5. A process according to claim 1 wherein the base in Step (b) is sodium hydroxide.

6. A process according to claim 1 wherein in Step (c) the compound of Formula III is treated with thionyl chloride and pyridine in acetonitrile.

7. A process according to claim 1 wherein in Step (c) 5-aminotetrazole and triethylamine are added in acetonitrile.

8. A process according to claim 1 wherein the solvent in Step (d) is isopropanol.

* * * * *